(12) United States Patent  (10) Patent No.: US 6,835,935 B2
Engdahl et al.                (45) Date of Patent:    Dec. 28, 2004

(54) SYSTEM AND METHOD FOR CALIBRATING AND TUNING A GAMMA CAMERA

(75) Inventors: John C. Engdahl, Lake Forest, IL (US); James F. Caruba, Bartlett, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 162 days.

(21) Appl. No.: 10/224,322

(22) Filed: Aug. 21, 2002

(65) Prior Publication Data

US 2004/0036026 A1 Feb. 26, 2004

(51) Int. Cl.⁷ ............................................. G01T 1/161
(52) U.S. Cl. ............................. 250/363.09; 250/252.1; 250/363.02
(58) Field of Search ..................... 250/363.09, 363.02, 250/252.1, 363.01, 361 R, 336.1; 378/207

(56) References Cited

U.S. PATENT DOCUMENTS

| | | | | |
|---|---|---|---|---|
| 3,011,057 A | | 11/1961 | Anger | |
| 4,079,257 A | * | 3/1978 | Jatteau et al. | 250/363.07 |
| 4,256,960 A | * | 3/1981 | Snider | 250/252.1 |
| 4,517,460 A | * | 5/1985 | Meulenbrugge et al. | 250/252.1 |
| 5,345,082 A | * | 9/1994 | Engdahl et al. | 250/363.07 |
| 5,610,396 A | * | 3/1997 | Mattern | 250/252.1 |
| 5,646,408 A | * | 7/1997 | Goldberg et al. | 250/363.07 |
| 5,847,395 A | * | 12/1998 | Malmin et al. | 250/363.07 |
| 6,342,698 B1 | * | 1/2002 | Stark | 250/363.09 |
| 6,452,164 B1 | * | 9/2002 | Andarawis et al. | 250/252.1 |
| 6,664,542 B2 | * | 12/2003 | Ye et al. | 250/363.04 |

\* cited by examiner

*Primary Examiner*—David Porta
*Assistant Examiner*—Christine Sung (57) ABSTRACT

A gamma camera having a system for performing a quality control procedure with minimal to no intervention from a user of the camera. In one aspect, the gamma camera includes a relatively weak radioactive source positioned at a fixed or known location relative to the gamma camera scintillation crystal and positioned so that the entrance window side of the crystal is facing the source, wherein the photons emitted from the source have an energy that is below the energy of photons used for diagnostic imaging. The response of the gamma camera photo-multiplier tubes to the absorption events caused by the radioactive source when the camera is idle can be compared to a baseline response to determine whether one or more of the PMTs need to be adjusted.

21 Claims, 5 Drawing Sheets

| PMT 104 (1) | | | | |
|---|---|---|---|---|
| EVENT# | SOURCE 106 (1) | SOURCE 106 (2) | ... | SOURCE 106 (N) |
| 1 | 14 | 19 | | 43 |
| 2 | 15 | 11 | | 44 |
| ⋮ | | | | |
| X | 17 | 13 | | 44 |

| PMT 104 (2) | | | | |
|---|---|---|---|---|
| EVENT# | SOURCE 106 (1) | SOURCE 106 (2) | ... | SOURCE 106 (N) |
| 1 | 15 | 23 | | 63 |
| 2 | 15 | 25 | | 54 |
| ⋮ | | | | |
| X | 12 | 23 | | 64 |

⋮

| PMT 104 (N) | | | | |
|---|---|---|---|---|
| EVENT# | SOURCE 106 (1) | SOURCE 106 (2) | ... | SOURCE 106 (N) |
| 1 | 14 | 19 | | 43 |
| 2 | 15 | 11 | | 44 |
| ⋮ | | | | |
| X | 17 | 13 | | 44 |

SYSTEM AND METHOD FOR CALIBRATING AND TUNING A GAMMA CAMERA

BACKGROUND OF THE INVENTION

1. Field of the Invention

The present invention generally relates to a system and method for calibrating and tuning a gamma ray camera ("gamma camera").

2. Discussion of the Background

Gamma cameras are primarily used by Doctors who specialize in the field of nuclear medicine. Nuclear medicine is a unique medical specialty wherein gamma cameras are used in conjunction with very low-level radioactive materials (called radionuclides or radiopharmaceuticals) to generate images of the anatomy of organs, bones or tissues of the body. Gamma cameras can also generate images that can be used to determine whether an organ is functioning properly.

The radionuclides or radiopharmaceuticals are introduced orally or intravenously into the body of a patient. Radiopharmaceuticals are specially formulated to collect temporarily in a certain part of the body to be studied, such as the patient's heart or brain. Once the radiopharmaceuticals reach the intended organ, they emit gamma rays that are then detected and measured by the gamma camera. The basic camera sold commercially for nuclear medical imaging is still similar to the original invention by Anger (U.S. Pat. No. 3,011,057, which is incorporated by reference herein).

A gamma camera includes a large area scintillation crystal, which functions as a gamma ray detector. The crystal is typically sodium iodide doped with a trace of thallium (NaI(Tl)). The crystal converts high-energy photons (e.g., gamma rays and X-rays) into visible light (i.e., lower energy photons). The crystal is positioned to receive a portion of the gamma ray emissions from the radiopharmaceuticals.

When a gamma ray strikes and is absorbed in the scintillation crystal, the energy of the gamma ray is converted into flashes of light (i.e., a large number of scintillation photons) that emanate from the point of the gamma ray's absorption in the scintillation crystal. A photo-multiplier tube (PMT), which is optically coupled to the scintillation crystal, detects a fraction of these scintillation photons and produces an output electronic signal (e.g., current or voltage pulse) having an amplitude that is proportional to the number of detected scintillation photons. The gamma ray camera typically has several photomultiplier tubes placed in a two dimensional array, with the signals from the different photomultiplier tubes being combined to provide an indication of the positions and energies of detected gamma rays.

The scintillation photons emitted from the detector crystal are typically in the visible light region of the electromagnetic spectrum (with a mean value of about 3 eV for NaI(Tl)). The scintillation photons spread out from the point of emission. A large fraction of the scintillation photons are transported from the point of emission to a light sensitive surface, called the photocathode, of the PMTs. A fraction of the scintillation photons incident on the photocathodes cause an electron to be emitted from the photocathode.

The electron, also called a photoelectron, is then electrostatically accelerated into an electron multiplying structure of the PMT, which causes an electrical current (or voltage) to be developed at an output of the PMT. The amplitude of the electrical signal is proportional to the number of photoelectrons generated in the PMT during the time period that scintillation photons are being emitted. Thus, after a gamma ray absorption event, the PMT outputs an electrical signal that can be used with other signals from other PMTs to determine the location of the gamma ray absorption event.

The number of scintillation photons producing electrical signals in each PMT is inversely related to the distance of the PMT from the point of gamma ray absorption, or event location. It is because of this relationship that the position of the event can be calculated from the signals of the PMTs surrounding the event location.

Ideally, the signal derived from each PMT should have exactly the same proportional relationship to the distance from the event location as for all other PMTs. The amplitudes of the signals derived from each PMT are proportional to two basic factors: 1) the number of scintillation photons detected by a PMT, and 2) the gain or amplification of the PMT. The accuracy to which the position of the event location can be calculated depends on these two factors remaining constant in time.

Typically, a gamma camera is tuned prior to its operation so as to ensure that the camera will calculate accurately the positions of event locations anywhere within an area called the field of view (FOV). Commercial, large field of view gamma cameras have between 50 and 100 PMTs. A tuning procedure will typically require a number of steps that balance or equalize the signal amplitudes of the PMTs. The gains of the PMTs are adjusted such that the sum of the signals from all the PMTs are approximately equal in response to a fixed energy gamma event, regardless of the location of the event.

A known pattern of event locations are presented to the camera, usually by placing a mask of precisely spaced lines or holes over the camera crystal, so that event location calculations can be calibrated to give the known locations fixed by the positions of the holes or slits, where the gammas can pass through the mask. The exact tuning and/or calibration steps may be different among cameras produced by different manufacturers. However, once the tuning and calibration steps are complete, the image quality, which is incumbent on the camera's ability to accurately position event locations, depends on the transport of scintillation light to the PMTs and the gains of the PMTs remaining unchanged from the time when the tuning and calibration procedures were performed.

A number of factors can cause a change in either the gain of a PMT or the light collection properties of the camera. PMT gain is a strong function of temperature, counting rate (i.e. the number event signals per unit time), and the high voltage (HV) power supply regulation. Additionally, PMTs change their gain over time as they age. The light collection from the crystal to the photocathodes of the PMTs can change if the transmissive properties of surfaces change. For example, the PMTs are optically coupled to a glass or plastic lightpipe using either an optical grease or epoxy. If any of these materials' light transmission properties change, then the transport of scintillation photons to the PMT will change. Additionally, NaI(Tl) is a hygroscopic material, and if water vapor reaches the crystal it becomes yellow and the light transmission is diminished.

Different manufacturers have developed and implemented different means to maintain the constancy of PMT gains. These means fall into two categories: 1) automatic (i.e. not requiring the user to initiate the process), and 2) user quality control (QC) procedures (i.e. procedures initiated by the user). Generally, a combination of both automatic and QC procedures is required.

One automatic system, for example, utilizes light emitting diodes (LEDs) coupled into the photomultiplier tubes to provide a light signal for calibration of each individual tube. A constant fraction of the light emitted by the LED is incident on the light sensitive photocathode of the PMT. The PMT output signal is checked against a reference that was set at the time of the last calibration. The gain of the PMT is adjusted if the measured signal has strayed from the reference.

This gain calibration technique depends on the light emitting diodes having a constant light output for each pulse. Light emitting diodes, however, do not have constant light output as a function of temperature, and may also vary over the lifetime of the diode. Another drawback of this technique of automatic calibration is that the light from the diode is mostly directly incident on the photocathode of the photomultiplier tube. Therefore, the transport of the light through the scintillation crystal, and associated optical elements, is not significantly sampled by the pulse of light from the diode.

User initiated QC procedures usually require the placement of a radioactive source to uniformly illuminate the camera. The system acquires an appropriate number of events to achieve statistically significant sampling of each event location. A computer program then analyzes the measured energies and/or image of event locations to determine whether or not the system has drifted away from the properly calibrated state. Many variations of this procedure are possible, but all require the user to position a source of radioactivity and initiate the computer controlled acquisition and analysis. Additionally, the procedures also typically require the user to remove the collimator from the camera.

QC procedures are cumbersome to the user. If they can be initiated at the end of the day, and complete themselves automatically, then the user's time required is minimal. However, radioactive sources that must be left out in a room overnight require institutional procedures for securing the room, logging out the source and returning it in the morning, and prohibiting access to the room by cleaning and unauthorized personnel. Performing QC procedures during working hours reduces available patient imaging time on the system and increases costs because personnel are not doing patient imaging.

SUMMARY OF THE INVENTION

The above described and other disadvantages are addressed by the present invention through the use of a system and method that is designed to calibrate and tune a gamma camera with minimal or no human intervention. The present invention provides a valuable feature for the user in that the user is assured of optimal performance of the camera without requiring laborious procedures and time that might otherwise be devoted to patient imaging.

Advantageously, with the present invention, analysis of PMT output pulses and calibration can be totally automatic. First, in one embodiment, the user does not need to place a radioactive source because such sources can be made part of the camera. Second, the system computer can be programmed to monitor continuously the count rate and, thereby, determine when the system is being used and when the system is idle. When the system is idle (i.e., the count rate is approximately equal to the natural background plus the contribution of the radioactive sources), the system computer can automatically monitor and record individual PMT signals. When a sufficient number of data points have been stored for each PMT, the mean amplitude and variance of each tube's response to the events can be calculated. These calculated values may be compared to baseline values (e.g., values that were calculated at the time of the last tuning and calibration of the system, providing a database for comparison) and/or to calculated values associated with neighborhing PMTs to determine whether and to what extent adjustments to the camera need to made. Further, the software may be programmed to analyze the results of the comparisons and automatically make the necessary PMT gain adjustments.

The above and other features and advantages of the present invention, as well as the structure and operation of preferred embodiments of the present invention, are described in detail below with reference to the accompanying drawings.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person skilled in the pertinent art to make and use the invention. In the drawings, like reference numbers indicate identical or functionally similar elements. Additionally, the left-most digit(s) of a reference number identifies the drawing in which the reference number first appears.

DETAILED DESCRIPTION OF THE PREFERRED EMBODIMENTS

While the present invention may be embodied in many different forms, there is described herein in detail an illustrative embodiment(s) with the understanding that the present disclosure is to be considered as an example of the principles of the invention and is not intended to limit the invention to the illustrated embodiment(s).

Figure 1:
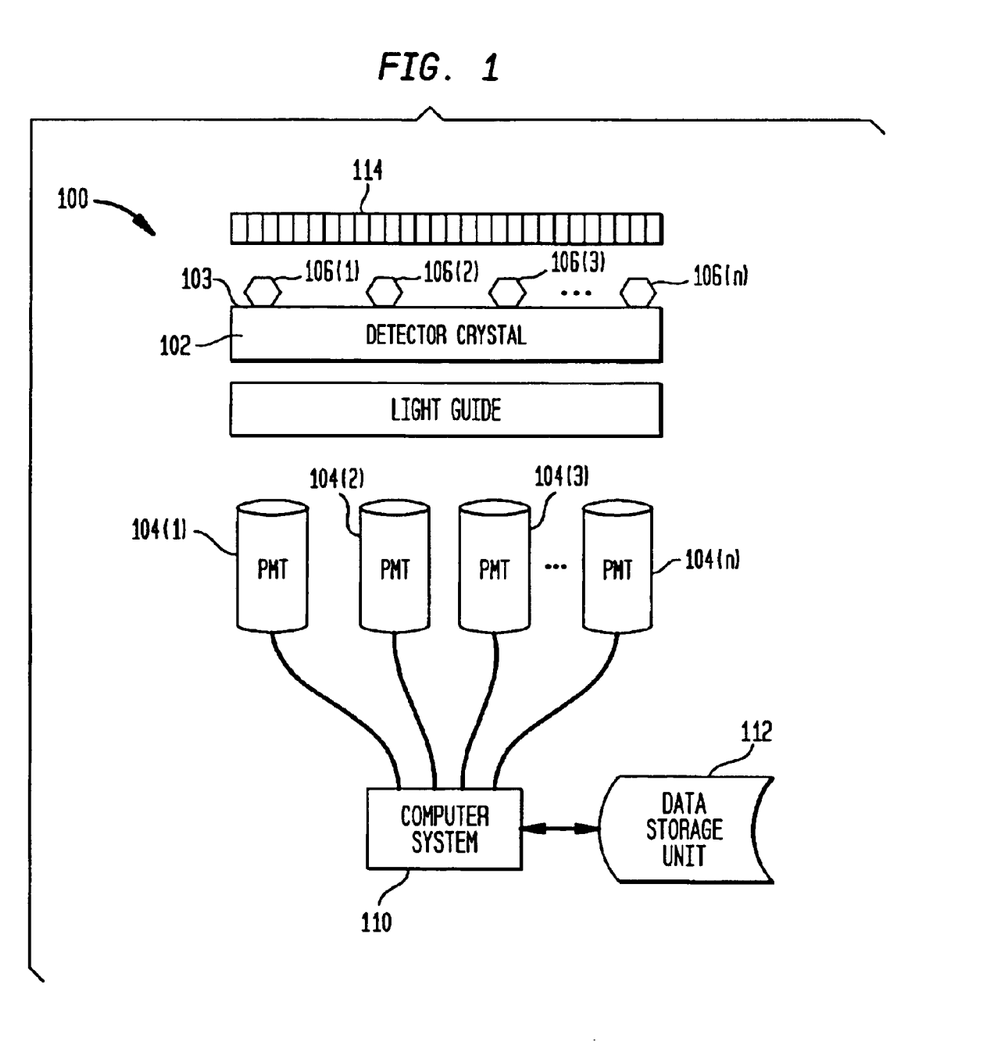
FIG. 1 is a diagram illustrating certain components of a gamma camera according to one embodiment of the present invention.

FIG. 1 is a diagram illustrating certain components of a gamma camera 100 according to one embodiment of the present invention. As shown in FIG. 1, gamma camera 100 includes a scintillation crystal 102 (or "detector crystal 102"), a number of photomultiplier tubes (PMTs) 104(a) . . . (n), and a computer system 110 coupled to the output of each PMT 104. Advantageously, one or more very weak radioactive sources 106(a) . . . (n) is placed so as to be facing an entrance window side 103 of scintillation crystal 102 at fixed or known locations. Gamma camera 100 may also include a collimator 114 and a light guide 116. In one embodiment, sources 106 are positioned between collimator 114 and crystal 102.

In one embodiment, sources 106 are positioned adjacent to the entrance window side 103 of scintillation crystal 102 at fixed or known locations. In a preferred embodiment, sources 106 are permanently or detachably affixed to entrance window side 103 of scintillation crystal 102 or to another component of camera 100, such as collimator 114. In a particular embodiment, a user of the camera 100 need not manually position sources 106 to occupy the fixed locations. For example, the sources may be pre-positioned and affixed to a component of camera 100 as part of the manufacturing process of the camera.

Sources 106 are chosen to have a photon energy that is below the source energies typical of diagnostic imaging, which are typically at least 140 keV. The source activity is also chosen to be below the limits set by regulatory agencies which would require licensing and inventory control. For example, Americium-241 (Am-241) emits a 60 keV X-ray and a long half-life. For activity levels less than 10 nCi, (nanocuries) such sources do not require radioactive material licenses.

Each radioactivity source 106, which is placed in a fixed location, causes scintillation photons to emanate from a small region directly "below" the source whenever an X-ray from the source 106 enters crystal 102. The scintillation photons produced by the X-rays will produce electronic signals of small amplitude in the photomultiplier tubes 104. Since the source activity is small, the probability of two absorption events overlapping in time is of negligible consequence.

The scintillation photons generated from each absorption event can be assumed to be located at a known point in the crystal 102 because each source 106 is placed in a fixed location and the range of the low energy photons (i.e., X-rays) within the scintillation crystal is short (e.g., <1 mm). Additionally, the mean number of scintillation photons produced from each X-ray absorption event will be near constant. Therefore, the signals produced in nearby PMTs, resultant from a number of scintillation photons generated from a single, monoenergetic X-ray absorption and subsequently transported to the PMTs, will be random statistical variants about constant means, modified by any changes in light transport and PMT response and amplification (i.e. gain).

Figure 2:
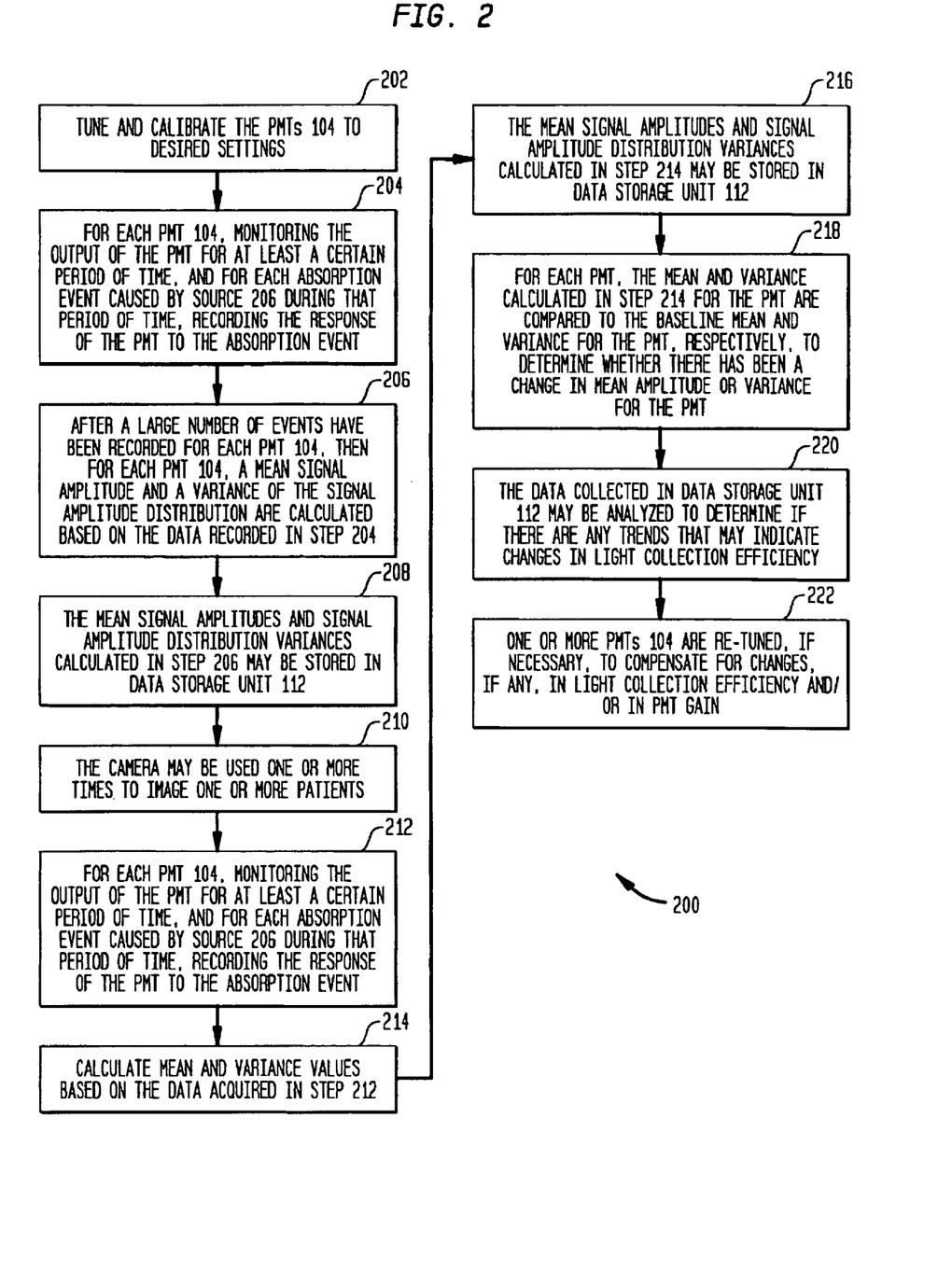
FIG. 2 is flow chart illustrating a process, according to one embodiment, for tuning the gamma camera.

Because the PMT output signal caused by one of the sources 106 should be a random statistical variant about a constant mean, absent changes in light collection and absent changes in the PMT itself, a process 200, which is illustrated in FIG. 2, can be used to determine whether such changes have occurred and can be used tune PMTs 104 to compensate for the changes. Process 200 assumes a single source 106, but multiple sources may be used.

Process 200 begins in step 202, where PMTs 104 are tuned and calibrated to desired settings. Step 204 requires, for each PMT 104, monitoring the output of the PMT for at least a certain period of time (e.g., one or more hours, but usually several hours) and, for each absorption event caused by source 106 during that period of time, recording the response of the PMT to the absorption event (i.e., recording the amplitude of the PMT output signal in response to the absorption event) so that a mean signal amplitude and a variance of the signal amplitude distribution for the PMT 104 can be calculated.

In step 206, after a large number of events have been recorded for each PMT 104, then, for each PMT 104, a mean signal amplitude and a variance of the signal amplitude distribution are calculated based on the data recorded in step 204. The mean signal amplitudes and signal amplitude distribution variances calculated in step 206 are the baseline means and variance values for PMTs 104. In step 208, the mean signal amplitudes and signal amplitude distribution variances calculated in step 206 may be stored in data storage unit 112.

In step 210, camera 100 may be used one or more times to image one or more patients. Like step 204, step 212 requires, for each PMT 104, monitoring the output of the PMT for at least a certain period of time and, for each absorption event caused by source 106 during that period of time, recording the response of the PMT to the absorption event. In step 214, for each PMT 104, mean and variance values are calculated based on the data acquired in step 212. In step 216, the mean signal amplitudes and signal amplitude distribution variances calculated in step 214 may be stored in data storage unit 112.

In step 218, for each PMT 104, the mean and variance calculated in step 214 for the PMT are compared to the baseline mean and variance for the PMT, respectively, to determine whether there has been a change in mean amplitude or variance for the PMT. Additionally, in step 220, the data collected in data storage unit 112 may be analyzed to determine if there are any data trends that may indicate changes in light collection efficiency. After step 220, control may pass back to step 210 or proceed to step 222. In step 222, one or more PMTs 104 are re-tuned, if necessary, to compensate for changes, if any, in light collection efficiency and/or in PMT Gain. After step 222, control may pass back to step 204 or 210.

A change in the mean amplitude of a particular PMT 104 may be indicative of a gain change in the PMT or change in light collection efficiency. Increases in mean amplitude are almost certainly indicative of a gain change, as it unlikely that light collection could increase. Global changes in mean amplitudes of the PMT's could be due to high voltage supply drift. Changes in an individual PMT where the amplitudes of the individual PMT's neighboring PMTs remain constant, would indicate a gain change of a single a single PMT (i.e., the individual PMT).

Changes in light collection efficiency are likely to affect more than one PMT. Changes in light collection efficiency are also likely to occur slowly, over a long period of time (weeks to months). Measured changes in the PMTs' responses are not likely to all be the same, but they will trend the same in time, so they should be recognizable as changes in light collection.

The variance of the amplitude distribution may be an indicator of light collection changes. Since the number of scintillation photons created by a single absorption event is a Poisson process, then the number of scintillation photons reaching a particular photocathode is also Poisson. If light collection does not change, then the variance in the distribution of acquired signal amplitudes should be predictable from random counting statistics. For example, if the mean number of scintillation photons reaching a photocathode is 100, then the standard deviation should be 10 (which is the square root of the variance which is equal to the mean for a Poisson distribution with a mean greater than 20) (Ref. G. F. Knoll, Radiation Detection and Measurement, $2^{nd}$ Edition, John Wiley and Sons, 1989, pp. 74–75). Since the gain of a PMT has an extremely good signal to noise ratio, a gain change will shift the mean of the distribution of amplitudes, but should not change the standard deviation of the distribution, as measured relative to the mean. If, however, the number of scintillation photons reaching the PMT changes (i.e., there is a change in light collection efficiency), then the standard deviation of the distribution will change, as measured relative to the mean value. Changes in light collection of greater than 10% should be recognizable when signal distributions of statistical precision of about 1% are acquired and analyzed.

Figure 3:
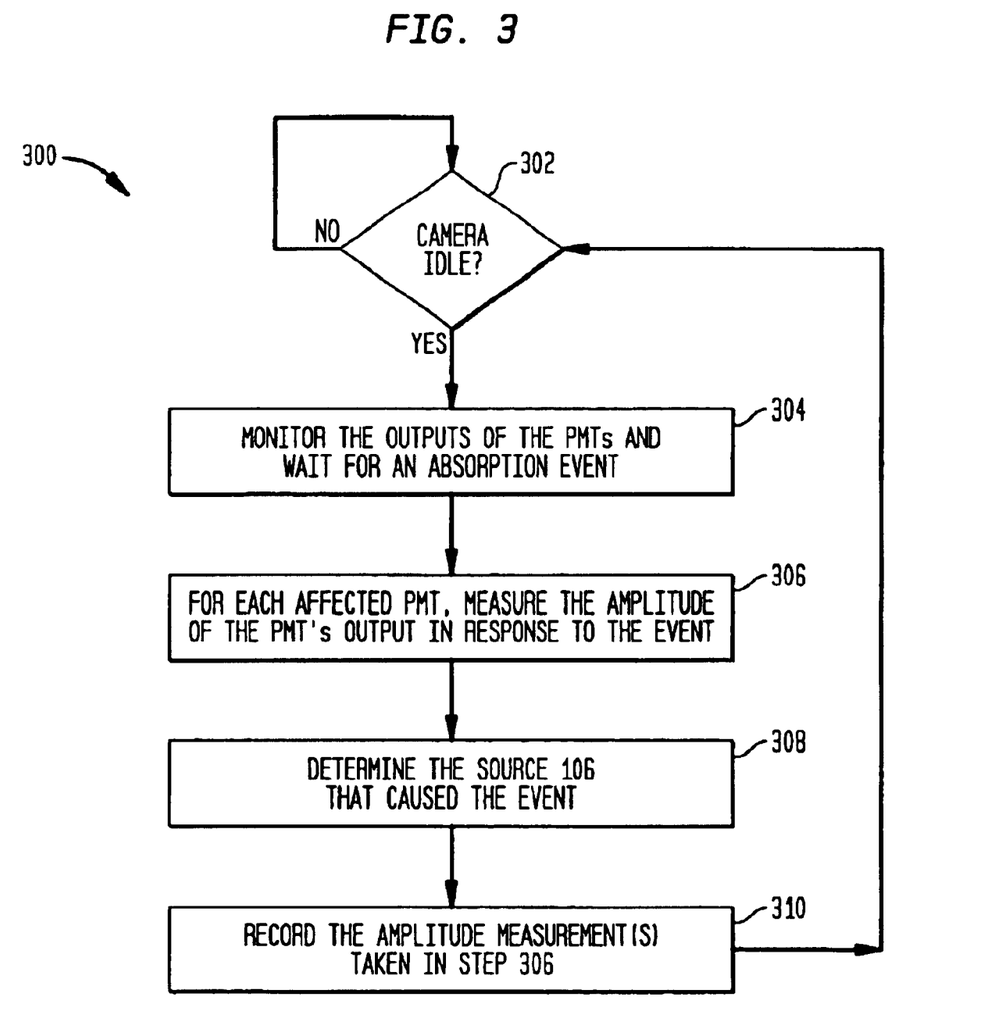
FIG. 3 is a flow chart illustrating a data gathering process according to one embodiment.

Referring now to FIG. 3, FIG. 3 is a flow chart illustrating a data gathering process 300, according to one embodiment of the invention, for gathering data that is used in tuning and calibrating gamma camera 100. Process 300 can be used to implement steps 204 and 212. Process 300 assumes that there may be more than one source 106.

Data gathering process 300 begins in step 302 where computer system 110 determines whether camera 100 is idle. Computer system 110 can determine whether camera 100 is idle by determining the count rate (e.g., the number of absorption events seen in a given period of time). The count rate is determined by monitoring the output of PMTs 104. If the determined count rate is approximately equal to the count rate expected from natural background radiation plus the contribution of the sources 106, then system 110 determines that camera 100 is idle. When camera 100 is determined to be idle, control passes to step 304, otherwise control passes back to step 302.

In step 304, system 110 monitors the outputs of PMTs 104 and waits for an absorption event. System 110 can be programmed to determine when an absorption event occurs because the output of each PMT in a group of PMTs that is located in a neighborhood surrounding the area where the event took place change at or about the same time as a result of the event. When an absorption event occurs, for each affected PMT 104, system 110 measures the magnitude of the PMT's output signal produced by the event (step 306). In step 308, system 110 determines the source 106 that caused the event by determining the location of the absorption event. Because the sources 106 are in a known, fixed location, there is a direct correlation between the location of an absorption event and the source 106 that produced the event.

In step 310, system 110 records the amplitude measurements taken in step 306. That is, for example, for each measurement, system 110 stores in data storage unit 112 a value corresponding to the measured amplitude and associates the value with the PMT 104 from which the measurement was taken and the source 106 that was determined in step 308. After step 310, control passes back to step 302.

Figure 4:
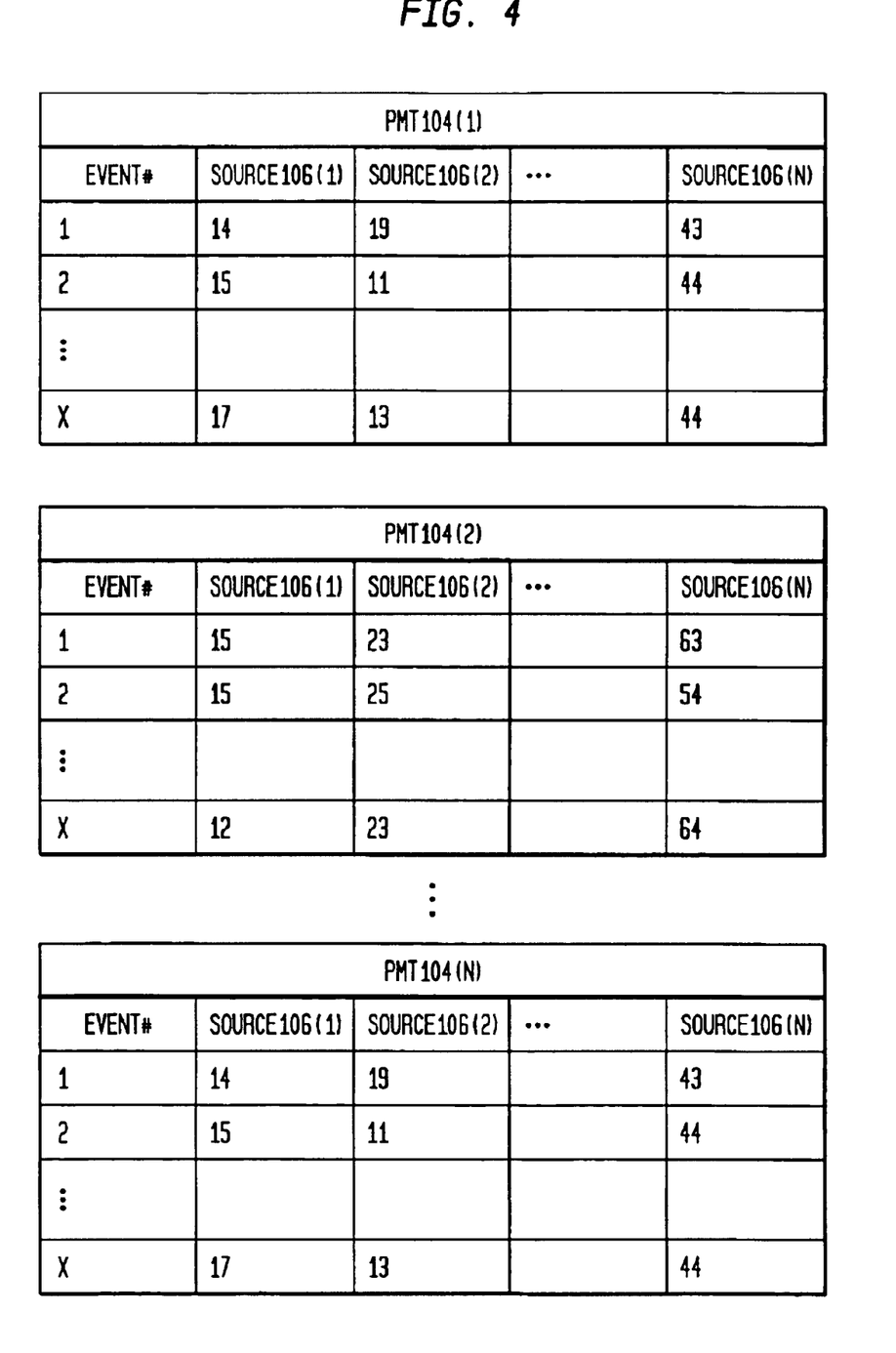
FIG. 4 illustrates a data structure for storing the data gathered during the data gathering process.

FIG. 4 illustrates a possible schema for storing the acquired data. As shown in FIG. 4, a data table 402 is provided for each PMT 104. From FIG. 4 one can determine, for each PMT, the magnitude of the output from the PMT from each recorded event from each source 106. For example, one can see that the magnitude of the output from PMT 104(1) caused by the second event from source 106(2) has a value of 11.

Figure 5:
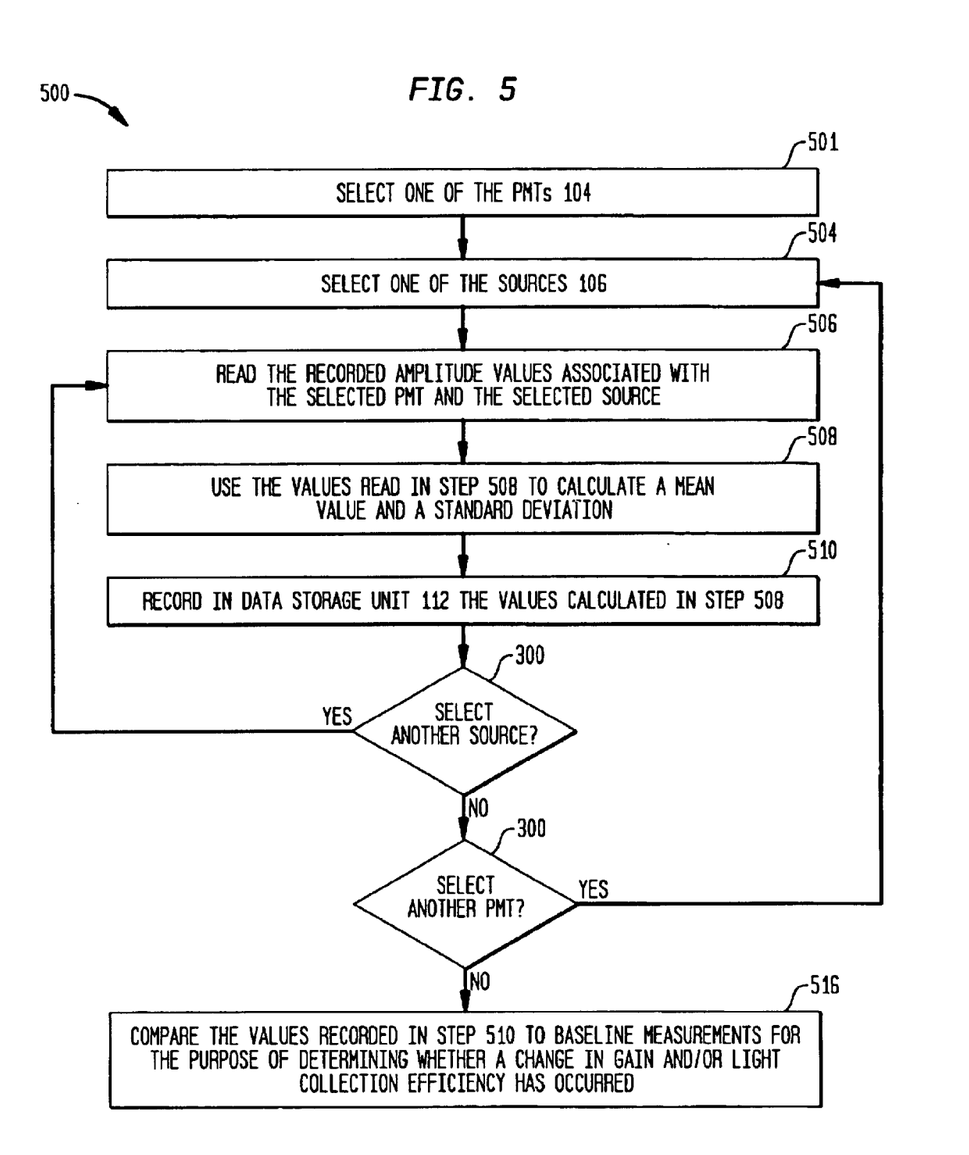
FIG. 5 is flow illustrating a data analysis process according to one embodiment.

Once data gathering process 300 has recorded a sufficient of amount of data (usually it takes at least a couple of hours to gather a sufficient amount of data), the process may end and a data analysis process 500 (see FIG. 5) may begin. FIG. 5 is a flow chart illustrating one embodiment of data analysis process 500. Process 500 may be used to implement steps 214–218 of process 200.

Data analysis process 500 begins in step 501, where system 110 selects one of the PMTs 104. In step 504, system 110 selects one of the sources 106. In step 506, system 110 reads the recorded amplitude values associated with the selected PMT and the selected source. In step 508, system 110 uses the values read in step 508 to calculate a mean value and a standard deviation. In step 510, system 110 records in data storage unit 112 the values calculated in step 508. In step 512, system 110 determines whether there is another source 106 to select. If there is, system 110 selects the source and control passes back to step 506, otherwise control passes to step 514. In step 514, system 110 determines whether there is another PMT 104 to select. If there is, system 110 selects another PMT and control passes back to step 504, otherwise control passes to step 516. In step 516, system 110 compares the values recorded in step 510 to baseline measurements for the purpose of determining whether a change in gain and/or light collection efficiency has occurred.

It should be apparent to a designer of gamma camera tuning and calibration procedures that the data provided from the accumulation of PMT responses to the sources 106 is a sensitive measure of light collection and PMT gains. The fact that the sources 106 are low energy provide a particular advantage because licensing and inventory control are not required. Additionally, The fact that the sources may remain in the camera even when the camera is being used to image a patient is another advantage because this relieves the user from having to place the sources manually each time the user desires to initiate quality control procedures. Further, the user need not manually initiate the quality control procedures as the system 110 can be programmed when the camera is idle and automatically initiate the quality control procedures. These and other advantages provide significant improvement over existing procedures and methods.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A gamma camera, comprising:
   a collimator;
   a scintillation crystal having an entrance window side;
   a radioactive source fixedly positioned at a known location relative to the crystal and positioned between said collimator and said crystal so that the entrance window side is facing the source, wherein the photons emitted from the source have an energy that is below the energy of photons used for diagnostic imaging; and
   a photo-multiplier tube (PMT) for detecting scintillation photons emitted from the scintillation crystal.

2. The gamma camera of claim 1, wherein the photons emitted from the source have a sufficiently low photon energy such that regulatory agencies do not require licensing or inventory control of the source.

3. The gamma camera of claim 1, wherein the source comprises Americium-241.

4. The gamma camera of claim 1, wherein the source consists essentially of Americium-241.

5. The gamma camera of claim 1, wherein the source is permanently attached to a component of the gamma camera.

6. The gamma camera of claim 1, wherein the source is permanently attached to the crystal.

7. The gamma camera of claim 1, further comprising a plurality of the radioactive sources.

8. A method for tuning a gamma camera having a photo-multiplier tube (PMT), a collimator, a scintillation crystal, and a source of radioactivity fixed between said collimator and said crystal, wherein the photons emitted from the source have an energy that is below the energy of photons used for diagnostic imaging, comprising:
   monitoring an output of the PMT for a period of time when the camera is idle;
   for each absorption event caused by the source of radioactivity during the period of time, recording the amplitude of an output pulse produced by the PMT at said output in response to the absorption event;

calculating a mean pulse amplitude based on the recorded amplitudes; and comparing said calculated mean pulse amplitude to a baseline value.

9. The method of claim 8, wherein the recorded amplitudes have a distribution and the method further comprises calculating a variance of the amplitude distribution.

10. The method of claim 9, further comprising comparing said calculated variance to a baseline variance.

11. The method of claim 10, wherein, prior to the step of monitoring the output of the PMT, the method includes the step of determining whether the gamma camera is idle.

12. The method of claim 8, wherein the photons emitted from the source have a sufficiently low photon energy such that regulatory agencies do not require licensing or inventory control of the source.

13. The method of claim 8, wherein the source comprises Americium-241.

14. The method of claim 8, wherein the source consists essentially of Americium-241.

15. A method for tuning a gamma camera having a plurality of photo-multiplier tubes (PMTs), a scintillation crystal, and a plurality of radioactivity sources, wherein the photons emitted from the sources have an energy that is below the energy of photons used for diagnostic imaging, comprising:

determining whether the gamma camera is idle; and performing the following acts after determining that the gamma camera is idle:

(A) detecting an absorption event caused by one of the plurality of sources;

(B) determining the source that caused the event;

(C) for each PMT affected by the event, measuring the amplitude of an output pulse produced by the PMT in response to the event, recording a value corresponding to the measured amplitude, and associating the value with the determined source and the PMT; and (D) repeating steps (A)–(C) at least a predetermined number of times or for at least a predetermined amount of time.

16. The method of claim 15, wherein after performing step (D), the method further comprises:

selecting one of the plurality of PMTs;

selecting one of the plurality of sources;

reading the set of recorded values that are associated with the selected source and the selected PMT;

calculating the mean of said values; and comparing the calculated mean to a baseline mean.

17. The method of claim 16, wherein the set of recorded values that are associated with the selected source and the selected PMT have a distribution and the method further comprises calculating a variance of the distribution.

18. The method of claim 17, further comprising comparing said calculated variance to a baseline variance.

19. The method of claim 15, wherein the photons emitted from the source have a sufficiently low photon energy such that regulatory agencies do not require licensing or inventory control of the source.

20. The method of claim 15, wherein the source comprises Americium-241.

21. The method of claim 15, wherein the source consists essentially of Americium-241.

* * * * *